US012347560B2

(12) United States Patent
Hashimoto (10) Patent No.: US 12,347,560 B2
(45) Date of Patent: Jul. 1, 2025

(54) PROGRESSION PREDICTION APPARATUS, PROGRESSION PREDICTION METHOD, AND PROGRESSION PREDICTION PROGRAM (71) Applicant: FUJIFILM Corporation, Tokyo (JP)

(72) Inventor: Takayuki Hashimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 422 days.

(21) Appl. No.: 18/052,552

(22) Filed: Nov. 3, 2022

(65) Prior Publication Data

US 2023/0088616 A1 Mar. 23, 2023

Related U.S. Application Data (63) Continuation of application No. PCT/JP2021/014577, filed on Apr. 6, 2021.

(30) Foreign Application Priority Data

Jun. 4, 2020 (JP) ................................. 2020-097899

(51) Int. Cl.
G16H 50/20 (2018.01)
G06T 7/00 (2017.01)
G16H 30/40 (2018.01)

(52) U.S. Cl.
CPC ........... G16H 50/20 (2018.01); G06T 7/0012 (2013.01); G16H 30/40 (2018.01); *G06T 2207/30061* (2013.01)

(58) Field of Classification Search
CPC ...... G16H 50/20; G16H 30/40; G06T 7/0012; G06T 2207/30061

(Continued)

(56) References Cited

U.S. PATENT DOCUMENTS 7,949,166 B2   5/2011   Moriya et al.
8,160,333 B2   4/2012   Miyasa et al.
(Continued)

FOREIGN PATENT DOCUMENTS

JP   2003325458   11/2003
JP   2007287018   11/2007
(Continued)

OTHER PUBLICATIONS

"International Search Report (Form PCT/ISA/210) of PCT/JP2021/014577," mailed on Jun. 22, 2021, with English translation thereof, pp. 1-5.

(Continued)

Primary Examiner — Allen H Nguyen
(74) Attorney, Agent, or Firm — JCIPRNET (57) ABSTRACT A processor is configured to derive, with reference to a database in which a plurality of reference images are saved such that an interpretation result about an abnormal shadow included in each reference image of the plurality of reference images is associated with the reference image, a degree of similarity between a target image and each of the plurality of reference images; the processor is configured to analyze, for a similar reference image, among the plurality of reference images, for which the degree of similarity is greater than or equal to a predetermined threshold value, an interpretation result regarding the similar reference image to thereby derive progression information about an abnormal shadow included in the similar reference image; and the processor is configured to statistically analyze the progression information to thereby derive prediction information for predicting future progression of an abnormal shadow included in the target image.

15 Claims, 8 Drawing Sheets (58) Field of Classification Search
USPC .......................................................... 382/128
See application file for complete search history.

(56) References Cited

U.S. PATENT DOCUMENTS

| | | | |
|---|---|---|---|
| 8,958,612 B2 | 2/2015 | Miyasa et al. | |
| 9,852,269 B2 | 12/2017 | Sakagawa et al. | |
| 10,297,352 B2 | 5/2019 | Sakagawa et al. | |
| 11,062,443 B2 | 7/2021 | Kanada | |
| 11,833,329 B2* | 12/2023 | Lee | G16H 50/30 |
| 2004/0249270 A1* | 12/2004 | Kondo | G06T 7/12 |
| | | | 382/128 |
| 2020/0365272 A1* | 11/2020 | Hattori | G16H 50/50 |
| 2021/0020295 A1* | 1/2021 | Li | G16H 20/30 |
| 2021/0161506 A1* | 6/2021 | Ito | A61B 8/429 |
| 2023/0197239 A1* | 6/2023 | Kaneko | G16H 50/20 |
| | | | 705/2 |
| 2024/0159738 A1* | 5/2024 | Yamasaki | G16H 50/20 |

FOREIGN PATENT DOCUMENTS

| | | |
|---|---|---|
| JP | 2007287027 | 11/2007 |
| JP | 2009095550 | 5/2009 |
| JP | 2010165127 | 7/2010 |
| JP | 2011118543 | 6/2011 |
| JP | 2011182960 | 9/2011 |
| JP | 2013010009 | 1/2013 |
| JP | 2020032044 | 3/2020 |

OTHER PUBLICATIONS

"Written Opinion of the International Searching Authority (Form PCT/ISA/237) of PCT/JP2021/014577," mailed on Jun. 22, 2021, with English translation thereof, pp. 1-8.

"Office Action of Japan Counterpart Application", issued on Aug. 15, 2023, with English translation thereof, p. 1-p. 5.

"Office Action of Japan Counterpart Application" with English translation thereof, issued on May 30, 2023, p. 1-p. 5.

* cited by examiner

| TYPES OF FINDINGS | FINDING SCORE |
|---|---|
| INFILTRATIVE SHADOW | 0.2 |
| GROUND-GLASS OPACITY | 0.7 |
| RETICULAR SHADOW | 0.9 (HIGHEST) |
| BRONCHODILATION | 0.3 |
| ... | ... |
| ... | ... |
| NORMAL LUNG | 0.1 |
| LOW-DENSITY AREA (EMPHYSEMA) | 0.1 |

Interstitial pneumonia that is 1 cm in size is observed in the right middle lobe of the lung.

Sr1

10/6/2018

Rr1

Interstitial pneumonia that is 1.5 cm in size is observed in the right middle lobe of the lung.

Sr2

4/2/2019

Rr2

Interstitial pneumonia that is 2.0 cm in size is observed in the right middle lobe of the lung.
A node is observed in the right upper lobe of the lung.

Sr3

10/11/2019

Rr3

Interstitial pneumonia that is 2.8 cm in size is observed in the right middle lobe of the lung.
A malignant node is observed in the right upper lobe of the lung.

PROGRESSION PREDICTION APPARATUS, PROGRESSION PREDICTION METHOD, AND PROGRESSION PREDICTION PROGRAM

CROSS-REFERENCE TO RELATED APPLICATIONS

This application is a Continuation of PCT International Application No. PCT/JP2021/014577 filed on Apr. 6, 2021, which claims priority under 35 U.S.C § 119(a) to Japanese Patent Application No. 2020-097899 filed on Jun. 4, 2020. Each of the above application(s) is hereby expressly incorporated by reference, in its entirety, into the present application.

BACKGROUND OF THE INVENTION

1. Field of the Invention

The present disclosure relates to a progression prediction apparatus, a progression prediction method, and a non-transitory computer recording medium storing a progression prediction program for predicting progression of abnormal shadows included in a medical image.

2. Description of the Related Art

With the recent advancement of medical apparatuses including CT (Computed Tomography) apparatuses and MRI (Magnetic Resonance Imaging) apparatuses, high-resolution three-dimensional images having higher quality have been used in diagnostic imaging.

Meanwhile, in the medical field, a technique for retrieving a past medical image similar to a target medical image, such as a CT image, that is an examination target has been proposed (see, for example, JP2020-032044A). In the technique described in JP2020-032044A, pixels of a medical image that is a diagnosis target are classified into a plurality of types of findings, and for each of the findings, a first feature value including the size and position of the finding is derived. In the technique, the degree of similarity is derived on the basis of the difference between the first feature value and a second feature value derived in advance for a saved medical image. When the degree of similarity is derived with the technique described in JP2020-032044A, a medical image, among a plurality of medical images saved in a database, similar to the target image can be retrieved. Further, a technique for identifying and outputting, for a retrieved similar image, a finding that contributes to the retrieval has been proposed (see, for example, JP2011-118543A).

SUMMARY OF THE INVENTION

In a diagnosis using a medical image, a follow-up may be done depending on the symptom and the treatment. In a case where a follow-up is done, the period until the next diagnosis is determined on the basis of the doctor's experience. However, in a case where the period until the next diagnosis that is too long, there is the possibility that the symptom progresses to be beyond cure. In contrast, in a case where the period until the next diagnosis is too short, there is the possibility that the patient is exposed to unnecessary radiation due to imaging performed although the symptom do not progress. Depending on the symptom, there may be a case where an area in which a new abnormal shadow appears as time passes can be predicted. In this case, when an area in which a new abnormal shadow appears can be predicted, some measures can be taken before the new abnormal shadow appears.

The present disclosure has been made in view of the above-described circumstances, and an object thereof is to allow the prediction of future progression of abnormal shadows included in a medical image that is a diagnosis target.

A progression prediction apparatus according to the present disclosure includes at least one processor, the processor being configured to derive, with reference to a database in which a plurality of reference images are saved such that an interpretation result about an abnormal shadow included in each reference image of the plurality of reference images is associated with the reference image, a degree of similarity between a target image and each of the plurality of reference images, analyze, for a similar reference image, among the plurality of reference images, for which the degree of similarity is greater than or equal to a predetermined threshold value, an interpretation result regarding the similar reference image to thereby derive progression information about an abnormal shadow included in the similar reference image, and statistically analyze the progression information to thereby derive prediction information for predicting future progression of an abnormal shadow included in the target image.

The "progression" includes a prognosis that is a medical forecast about the progression and consequence of the abnormal shadow. The "progression" covers a period until an examination carried out thereafter for the abnormal shadow.

In the progression prediction apparatus according to the present disclosure, the prediction information may include at least one of a disease name, a change in size of the abnormal shadow, a change in shape of the abnormal shadow, presence or absence of an appearance of a new abnormal shadow, a location where the new abnormal shadow appears, a name of a complication that is likely to develop, or a period until a next diagnosis.

In the progression prediction apparatus according to the present disclosure, the processor may be configured to display the prediction information on a display.

In the progression prediction apparatus according to the present disclosure, the processor may be configured to, in a case where the prediction information includes the location where the new abnormal shadow appears, display the target image so as to highlight, in the displayed target image, the location where the new abnormal shadow appears.

In the progression prediction apparatus according to the present disclosure, the processor may be configured to derive a feature value about the target image and derive the degree of similarity on the basis of the feature value derived for the target image and a feature value about each of the plurality of reference images.

In the progression prediction apparatus according to the present disclosure, the processor may be configured to derive a degree of similarity between a target image group and each of reference image groups, the target image group including the target image and at least one past target image acquired on an imaging date earlier than an imaging date of the target image by imaging a photographic subject the same as a photographic subject for which the target image is acquired, each of the reference image groups including, among the plurality of reference images, a plurality of reference images acquired by imaging a same photographic subject and each having an imaging interval corresponding to imaging intervals of the target image and the at least one past target image, and analyze, for a similar reference image group for which the degree of similarity is greater than or equal to a predetermined threshold value, interpretation results associated with a plurality of similar reference images included in the similar reference image group to thereby derive progression information about the similar reference image group.

A progression prediction method according to the present disclosure includes: deriving, with reference to a database in which a plurality of reference images are saved such that an interpretation result about an abnormal shadow included in each reference image of the plurality of reference images is associated with the reference image, a degree of similarity between a target image and each of the plurality of reference images; analyzing, for a similar reference image, among the plurality of reference images, for which the degree of similarity is greater than or equal to a predetermined threshold value, an interpretation result regarding the similar reference image to thereby derive progression information about an abnormal shadow included in the similar reference image; and statistically analyzing the progression information to thereby derive prediction information for predicting future progression of an abnormal shadow included in the target image.

A non-transitory computer recording medium storing a program for causing a computer to perform the progression prediction method according to the present disclosure may be provided.

According to the present disclosure, the prediction of future progression of abnormal shadows included in a medical image that is a diagnosis target can be made.

DESCRIPTION OF THE PREFERRED EMBODIMENTS

Figure 1:
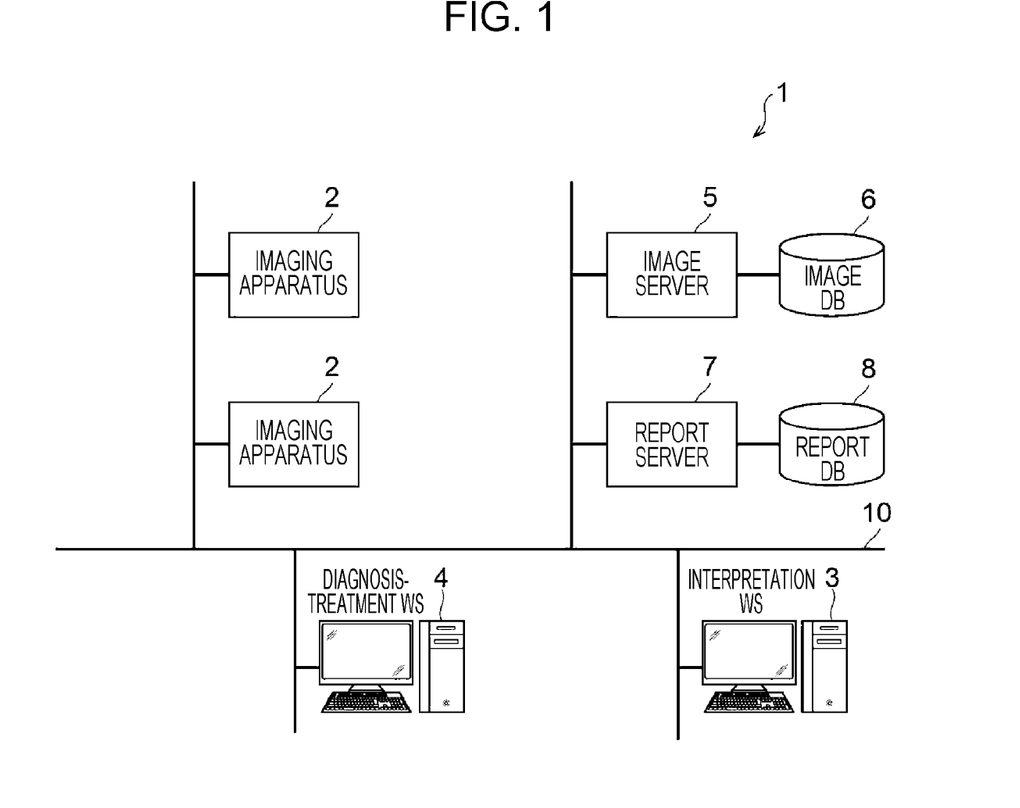
FIG. 1 is a schematic configuration diagram of a medical information system to which a progression prediction apparatus according to an embodiment of the present disclosure is applied.

Hereinafter, an embodiment of the present disclosure will be described with reference to the drawings. First, a configuration of a medical information system 1 to which a progression prediction apparatus according to the present embodiment is applied will be described. FIG. 1 is a schematic configuration diagram of the medical information system 1. The medical information system 1 illustrated in FIG. 1 is a system for, on the basis of an examination order made by a doctor of a diagnosis-treatment department using a publicly known ordering system, imaging an examination target area of a photographic subject, storing a medical image acquired by imaging, allowing an interpreting doctor to interpret the medical image and create an interpretation report, and allowing the doctor of the diagnosis-treatment department who has made the order to view the interpretation report and observe in detail the medical image that is an interpretation target.

As illustrated in FIG. 1, the medical information system 1 includes a plurality of imaging apparatuses 2, an interpretation WS (workstation) 3 that is an interpretation terminal, a diagnosis-treatment WS 4, an image server 5, an image database (hereinafter referred to as "image DB") 6, a report server 7, and a report database (hereinafter referred to as "report DB") 8, which are connected to each other via a wired or wireless network 10 so as to be able to communicate with each other.

Each of the apparatuses is a computer in which an application program for causing the apparatus to function as a configuration element of the medical information system 1 is installed. The application program is stored in a storage device of a server computer connected to the network 10 or in a network storage so as to be externally accessible, and in response to a request, downloaded to and installed in the computer. Alternatively, the application program is recorded to a recording medium, such as a DVD (digital versatile disc) or a CD-ROM (compact disc read-only memory) and distributed, and is installed in the computer from the recording medium.

The imaging apparatus 2 is an apparatus (modality) that images an area that is a diagnosis target of a photographic subject to thereby generate a medical image that shows the diagnosis target area. Specifically, the imaging apparatus 2 is, for example, a plain X-ray imaging apparatus, a CT apparatus, an MRI apparatus, or a PET (Positron Emission Tomography) apparatus. The medical image generated by the imaging apparatus 2 is transmitted to the image server 5 and saved in the image DB 6.

The interpretation WS 3 is a computer used by, for example, an interpreting doctor of a radiology department to, for example, interpret a medical image and create an interpretation report, and includes a progression prediction apparatus 20 according to the present embodiment. The interpretation WS 3 makes a request to view a medical image to the image server 5, performs various types of image processing for a medical image received from the image server 5, displays a medical image, accepts input of a finding remark about a medical image, and so on. The interpretation WS 3 performs an analysis process for a medical image and an input finding remark, supports creation of an interpretation report based on an analysis result, makes a request to register an interpretation report and a request to view an interpretation report to the report server 7, and displays an interpretation report received from the report server 7. These processes are performed by the interpretation WS 3 executing a software program for the processes.

The diagnosis-treatment WS 4 is a computer used by a doctor of a diagnosis-treatment department to, for example, observe an image in detail, view an interpretation report, and create an electronic medical chart, and includes a processing device, a display device such as a display, and an input device including a keyboard and a mouse. The diagnosis-treatment WS 4 makes a request to view an image to the image server 5, displays an image received from the image server 5, makes a request to view an interpretation report to the report server 7, and displays an interpretation report received from the report server 7. These processes are performed by the diagnosis-treatment WS 4 executing a software program for the processes.

The image server 5 is a general-purpose computer in which a software program for providing a database management system (DBMS) function is installed. The image server 5 includes a storage in which the image DB 6 is set up. This storage may be a hard disk apparatus that is connected to the image server 5 via a data bus or may be an NAS (Network Attached Storage) that is connected to the network 10 or a disk device that is connected to an SAN (Storage Area Network). When accepting a request from the imaging apparatus 2 to register a medical image, the image server 5 saves the medical image, puts the saved medical image into a database format, and registers the medical image to the image DB 6.

To the image DB 6, image data of a medical image acquired by the imaging apparatus 2 and accessory information are registered. The accessory information includes, for example, an image ID (identification) for identifying the individual medical image, a patient ID for identifying the photographic subject, an examination ID for identifying the examination, a unique ID (UID: unique identification) assigned on a medical image by medical image basis, the examination date and the examination time when the medical image is generated, the type of the imaging apparatus used in the examination for acquiring the medical image, patient information including the name, age, and sex of the patient, the examined area (imaged area), imaging information (the imaging protocol, the imaging sequence, the imaging method, imaging conditions, use of a contrast medium, and so on), and the series numbers or collection numbers when a plurality of medical images are acquired in a single examination. For a medical image for which an interpretation report is generated on the interpretation WS 3, identification information for identifying the generated interpretation report is registered to the image DB 6. With the identification information, a reference image saved on the image server 5 and an interpretation report saved on the report server 7 are associated with each other. To the image DB 6, feature values about the lung area included in a medical image, the feature values being derived upon generation of an interpretation report, are also registered. The feature values will be described below.

A medical image for which an interpretation report has been generated and that has been registered to the image DB 6 is referred to as "reference image" in the following description. A medical image for which an interpretation report will be generated is referred to as "target image".

When receiving a viewing request from the interpretation WS 3 or the diagnosis-treatment WS 4 via the network 10, the image server 5 retrieves a medical image registered to the image DB 6 and transmits the retrieved medical image to the interpretation WS 3 or the diagnosis-treatment WS 4 that has made the request.

In the report server 7, a software program that provides the functions of a database management system to general-purpose computers is installed. When accepting a request to register an interpretation report from the interpretation WS 3, the report server 7 saves the interpretation report, puts the saved interpretation report into a database format, and registers the interpretation report to the report DB 8.

To the report DB 8, the interpretation report created on the interpretation WS 3 and including a finding remark that is an interpretation result regarding the medical image is registered. The interpretation report may include, for example, the medical image that is an interpretation target, an image ID for identifying the medical image, an interpreting doctor ID for identifying the interpreting doctor who has made the interpretation, the name of a lesion, positional information of the lesion, and information for accessing the medical image that includes the lesion.

When receiving a request to view or transmit an interpretation report from the interpretation WS 3 or the diagnosis-treatment WS 4 via the network 10, the report server 7 retrieves the interpretation report registered to the report DB 8 and transmits the retrieved interpretation report to the interpretation WS 3 or the diagnosis-treatment WS 4 that has made the request. In the present embodiment, in response to a request made to the image server 5 to view a similar reference image derived as described below, an instruction for transmitting an interpretation report about the similar reference image is given to the report server 7 from the image server 5. Accordingly, the report server 7 transmits the interpretation report about the similar reference image to the interpretation WS 3 or the diagnosis-treatment WS 4 that has made the request.

It is assumed that the medical image in the present embodiment is a three-dimensional CT image of a lung, which is a diagnosis target, the CT image being formed of a plurality of tomographic images, and the CT image is interpreted to thereby create an interpretation report that includes, as a finding remark, an interpretation result regarding abnormal shadows included in the lung. Note that the medical image is not limited to a CT image, and any medical image, such as an MIII image or a plain two-dimensional image acquired by a plain X-ray imaging apparatus, can be used.

The network 10 is a wired or wireless local area network that connects various apparatuses in the hospital to each other. In a case where the interpretation WS 3 is installed in another hospital or a clinic, the network 10 may be configured so as to connect local area networks in the respective hospitals to each other via the Internet or a dedicated line.

Figure 2:
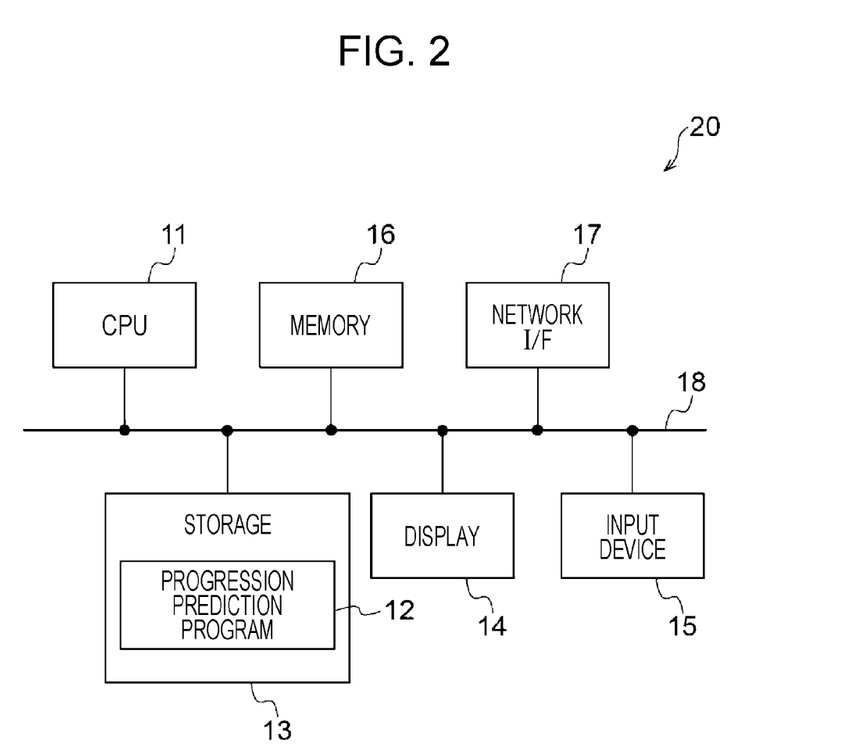
FIG. 2 is a schematic configuration diagram of the progression prediction apparatus according to the present embodiment.

Next, the progression prediction apparatus according to the present embodiment will be described. FIG. 2 illustrates a hardware configuration of the progression prediction apparatus according to the present embodiment. As illustrated in FIG. 2, the progression prediction apparatus 20 includes a CPU (central processing unit) 11, a nonvolatile storage 13, and a memory 16 that serves as a temporary storage area. The progression prediction apparatus 20 includes a display 14, which is, for example, a liquid crystal display, an input device 15 that includes a keyboard and a mouse, and a network I/F (interface) 17 that is connected to the network 10. The CPU 11, the storage 13, the display 14, the input device 15, the memory 16, and the network I/F 17 are connected to a bus 18. The CPU 11 is an example of a processor in the present disclosure.

The storage 13 is implemented as, for example, an HDD (hard disk drive), an SSD (solid state drive), or a flash memory. In the storage 13 that serves as a storage medium, a progression prediction program is stored. The CPU 11 reads a progression prediction program 12 from the storage 13, loads the progression prediction program 12 to the memory 16, and executes the loaded progression prediction program 12.

Figure 3:
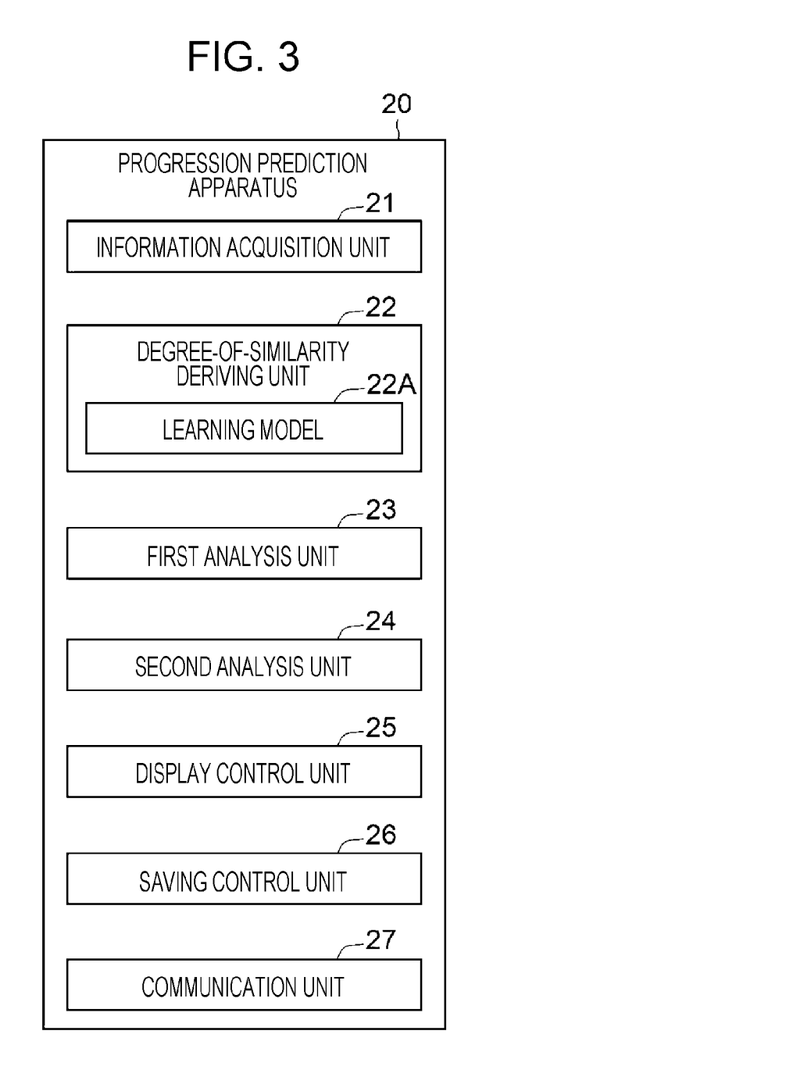
FIG. 3 is a functional configuration diagram of the progression prediction apparatus according to the present embodiment.

Next, a functional configuration of the progression prediction apparatus according to the present embodiment will be described. FIG. 3 is a functional configuration diagram of the progression prediction apparatus according to the present embodiment. As illustrated in FIG. 3, the progression prediction apparatus 20 includes an information acquisition unit 21, a degree-of-similarity deriving unit 22, a first analysis unit 23, a second analysis unit 24, a display control unit 25, a saving control unit 26, and a communication unit 27. When the CPU 11 executes the progression prediction program 12, the CPU 11 functions as the information acquisition unit 21, the degree-of-similarity deriving unit 22, the first analysis unit 23, the second analysis unit 24, the display control unit 25, the saving control unit 26, and the communication unit 27.

The information acquisition unit 21 acquires from the image server 5 a target image that is a target of interpretation in response to an instruction from the input device 15 given by an interpreting doctor who is an operator. The information acquisition unit 21 acquires feature values about reference images registered to the image DB 6 and saved on the image server 5 in order to derive the degrees of similarity described below. The information acquisition unit 21 acquires an interpretation report about a similar reference image derived as described below from the report server 7.

The degree-of-similarity deriving unit 22 derives the degrees of similarity between a target image and a plurality of reference images saved on the image server 5 with reference to the image DB 6. For this, the degree-of-similarity deriving unit 22 analyzes the target image to thereby classify each pixel of the lung area included in the target image into any of a plurality of predetermined findings. In the present embodiment, the degree-of-similarity deriving unit 22 has a learning model 22A that is subjected to machine learning so as to distinguish each pixel of the lung area included in a medical image with respect to each of the plurality of predetermined findings. One pixel may be classified into the findings, or a unit of a plurality of pixels may be classified into the findings.

In the present embodiment, the learning model 22A is subjected to learning so as to classify each pixel of the lung area included in the target image into a plurality of findings including, for example, an infiltrative shadow, a tumor shadow, ground-glass opacity, centrilobular nodular opacity, non-centrilobular nodular opacity, a punctate shadow, a reticular shadow, linear opacity, interlobular septum thickening, a cellular lung, a cyst, a low-density area (emphysema), an emphysema tendency, a vomica, pleural thickening, pleural effusion, bronchodilation, traction bronchodilation, blood vessels, a normal lung, the chest wall, and the mediastinum. Note that the types of findings are not limited to these and may be findings more than these or less than these.

In the present embodiment, the learning model 22A is formed of a convolutional neural network subjected to machine learning with, for example, deep learning by using training data so as to distinguish findings in a medical image.

The training data for learning by the learning model 22A is formed of combinations of medical images and pieces of ground truth data indicating the results of classifying into findings about the medical images. In response to input of a medical image, the learning model 22A outputs, for each pixel of the medical image, a finding score for each of the plurality of findings. The finding score is a score, for each finding, indicating the conspicuity of the finding. The finding score has a value of, for example, 0 or more and 1 or less, and the finding score having a larger value indicates that the finding is more conspicuous.

Figure 4:
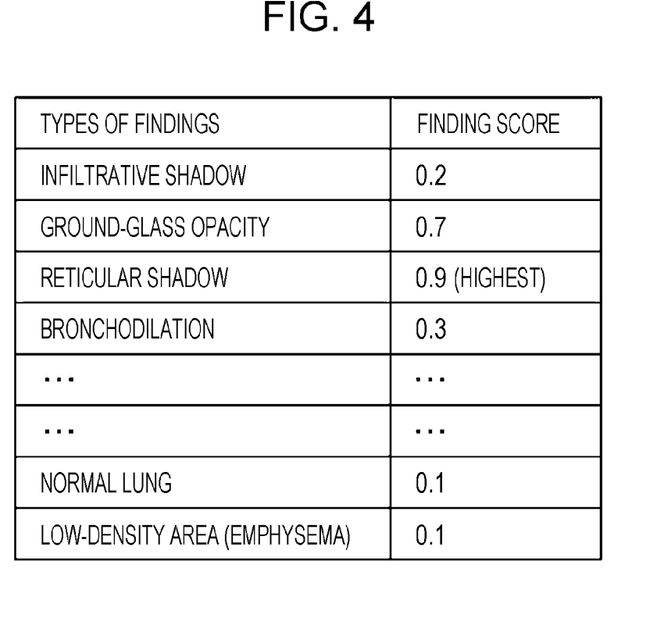
FIG. 4 is a diagram illustrating finding scores corresponding to the types of findings for a certain pixel.

FIG. 4 is a diagram illustrating finding scores corresponding to the types of findings for a certain pixel. To give a brief explanation, FIG. 4 illustrates evaluation values about some of the findings. In the present embodiment, the degree-of-similarity deriving unit 22 classifies an input pixel as a finding having the highest finding score among the finding scores for the respective findings output by the learning model 22A for the input pixel. For example, when the finding scores as illustrated in FIG. 4 are output, the possibility of the pixel being a reticular shadow is highest and the possibility of the pixel being ground-glass opacity is the next highest. In contrast, there is almost no possibility that the pixel is a normal lung or a low-density area. Therefore, when the finding scores as illustrated in FIG. 4 are output, the degree-of-similarity deriving unit 22 classifies the pixel as a reticular shadow for which the finding score is 0.9 and highest. When such a classification process is performed for all pixels in the lung area, every pixel in the lung area is classified as one of the plurality of types of findings.

The degree-of-similarity deriving unit 22 derives a feature value for each finding into which the target image is classified. Specifically, the degree-of-similarity deriving unit 22 calculates as the feature value, at least one of, for example, the position of the area of the finding, the size of the area of the finding, the average density of the finding, the density distribution of the finding, the number of areas corresponding to the finding, or the average size of the areas corresponding to the finding. Here, the feature value is normalized to a value of 0 or more and 1 or less. The feature values calculated for the target image are referred to as first feature values. For example, the size of the area of each finding, the number of areas corresponding to each finding, and the average size of the areas corresponding to each finding are size feature values. As the position of the area of each finding, the coordinate values of the position of the center of gravity of the area of the finding can be used. As the size of the area of each finding, the volume of the area of the finding can be used.

In the present embodiment, feature values about a plurality of reference images are registered to the image DB 6. The feature values registered to the image DB 6 for the reference images are referred to as second feature values. When first feature values are acquired for the target image, the target image is registered to the image DB 6 as a new reference image. At this time, the first feature values about the target image are registered to the image DB 6 as the second feature values for the new reference image.

When the same findings having substantially the same sizes are present at substantially the same positions in the target image and a reference image, the two images are medically similar to each other. The degree-of-similarity deriving unit 22 derives the degree of similarity between the target image and a reference image on the basis of the difference in distance between the first feature value for each finding derived for the target image and the second feature value for the finding registered to the image DB 6 for the reference image. The degree-of-similarity deriving unit 22 derives the degrees of similarity between the target image and all reference images registered to the image DB 6. For this, the degree-of-similarity deriving unit 22 first derives for each finding, the difference in distance between the first feature value and the second feature value for a reference image. For example, the degree-of-similarity deriving unit 22 derives as the difference in distance between the first feature value and the second feature value, the square sum of the differences in distance for the respective types of feature values or the sum of the absolute values of the differences in the distance for the respective types of feature values. The degree-of-similarity deriving unit 22 adds up or weights and adds up the differences in distance for the respective findings to thereby calculate the difference in distance between the target image and the reference image as the degree of similarity.

When the first feature value is equal to the second feature value, the difference in feature value is equal to zero. Therefore, in the present embodiment, the difference between the first feature value and the second feature value is given a minus sign. Accordingly, the derived degree of similarity has a larger value as the target image and the reference image are similar to each other to a larger degree.

The first analysis unit 23 identifies a similar reference image, among a plurality of reference images registered to the image DB 6, having a degree of similarity greater than or equal to a predetermined threshold value. The first analysis unit 23 analyzes an interpretation report about the similar reference image to thereby derive progression information about abnormal shadows included in the similar reference image. A process performed by the first analysis unit 23 will be described below.

The first analysis unit 23 identifies, with reference to the image DB 6, reference images of a photographic subject the same as a photographic subject for which the similar reference image is acquired. The first analysis unit 23 instructs the information acquisition unit 21 to acquire an interpretation report associated with the similar reference image and those associated with the identified reference images. Accordingly, the information acquisition unit 21 acquires the interpretation report associated with the similar reference image and those associated with the identified reference images from the report server 7. The acquired interpretation report corresponds to an interpretation result regarding the similar reference image in the present disclosure. The first analysis unit 23 analyzes the acquired interpretation reports to thereby derive progression information about abnormal shadows included in the similar reference image.

Figure 5:
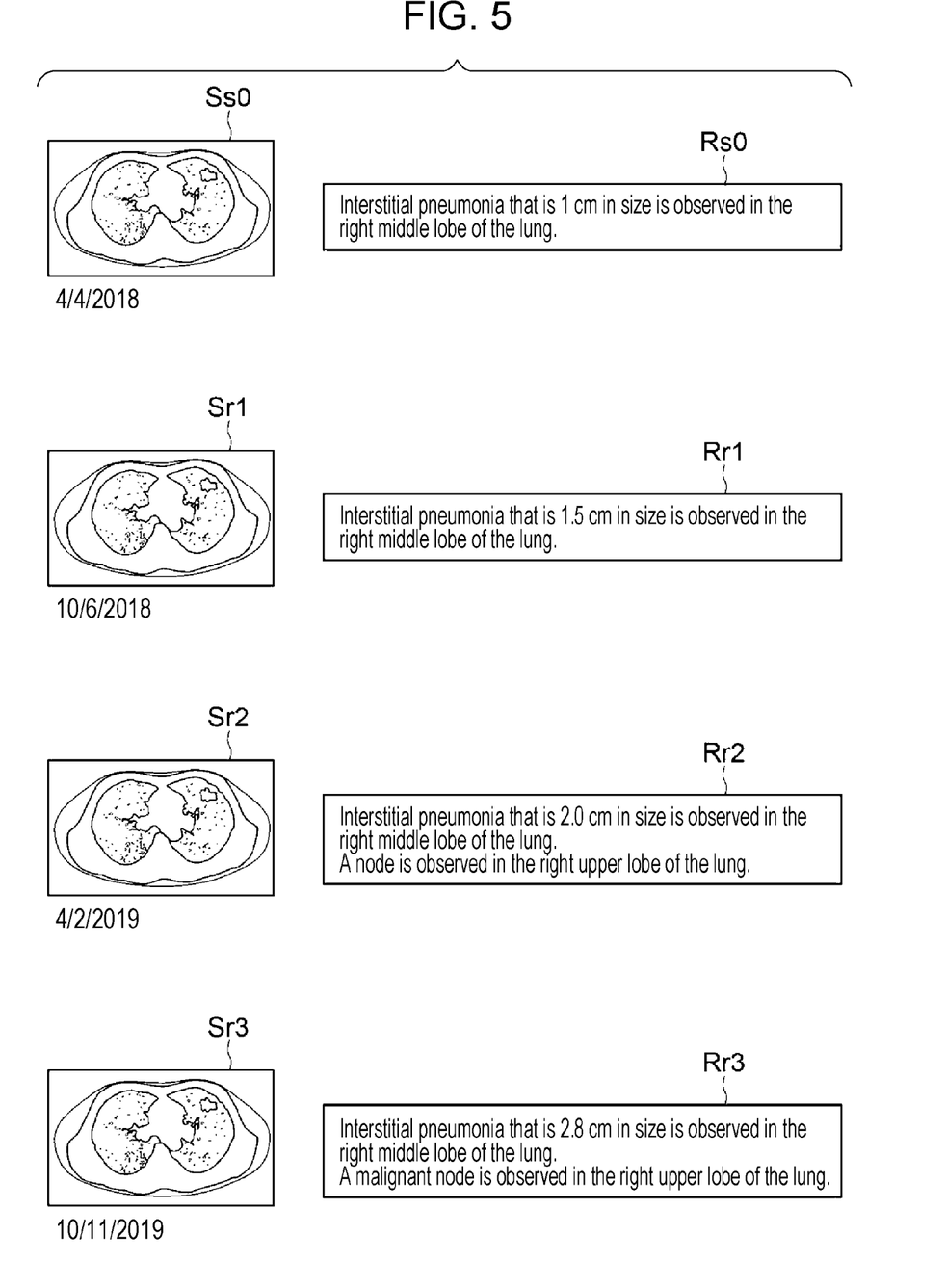
FIG. 5 includes diagrams schematically illustrating interpretation results regarding similar reference images.

FIG. 5 includes diagrams schematically illustrating interpretation results regarding similar reference images. As illustrated in FIG. 5, it is assumed that for a similar reference image Ss0, three reference images (hereinafter referred to as "related similar reference images") Sr1 to Sr3 of the same photographic subject are registered to the image DB 6. The imaging date of the similar reference image Ss0 is Apr. 4, 2018, and the imaging dates of the related similar reference images Sr1 to Sr3 are Oct. 6, 2018, Apr. 2, 2019, and Oct. 11, 2019 respectively. It is assumed that the similar reference image Ss0 and the related similar reference images Sr1 to Sr3 are associated with interpretation reports Rs0 and Rr1 to Rr3 respectively.

The content of the interpretation report Rs0 reads "interstitial pneumonia that is 1 cm in size is observed in the right middle lobe of the lung". The content of the interpretation report Rr1 reads "interstitial pneumonia that is 1.5 cm in size is observed in the right middle lobe of the lung". The content of the interpretation report Rr2 reads "interstitial pneumonia that is 2.0 cm in size is observed in the right middle lobe of the lung, and a node is observed in the right upper lobe of the lung". The content of the interpretation report Rr3 reads "interstitial pneumonia that is 2.8 cm in size is observed in the right middle lobe of the lung, and a malignant node is observed in the right upper lobe of the lung".

The first analysis unit 23 acquires, for all of the similar reference images, the interpretation reports about the similar reference images. The first analysis unit 23 analyzes the interpretation reports to thereby derive progression information about abnormal shadows included in the similar reference images and the related similar reference images. Specifically, the first analysis unit 23 identifies from the interpretation reports Rs0 and Rr1 to Rr3, for example, the imaging intervals of the similar reference image and the related similar reference images, descriptions each related to a change in size of an abnormal shadow, descriptions each related to a change in shape, descriptions each related to the location of a newly appearing abnormal shadow, and descriptions each related to the name of a complication. Based on the identified descriptions, the first analysis unit 23 derives at least one of, for example, the imaging intervals, the doubling time of an abnormal shadow, a changed shape, a location where a new abnormal shadow appears, or the name of a complication as progression information. The doubling time is the time taken for the size of an abnormal shadow to increase about two-fold.

The imaging intervals can be derived on the basis of the imaging intervals of the similar reference image Ss0 and the related similar reference images Sr1 to Sr3. The doubling time of an abnormal shadow can be derived from a description related to a change in size of the abnormal shadow. A changed shape can be derived from a description related to a change in shape. A location where a new abnormal shadow appears can be derived from a description related to the location of the newly appearing abnormal shadow. The name of a complication can be derived from a description related to the name of the complication. Accordingly, the first analysis unit 23 derives progression information about all of the similar reference images.

The second analysis unit 24 statistically analyzes the progression information derived by the first analysis unit 23 to thereby derive prediction information for predicting future progression of abnormal shadows included in the target image. In the present embodiment, the prediction information includes statistical information about at least one of, for example, the imaging interval until the next imaging, the doubling time of an abnormal shadow, a shape that will change in the future, a location where a new abnormal shadow will appear in the future, or the name of a complication that will develop in the future.

As the statistical information about the imaging interval until the next imaging, the second analysis unit 24 derives the most common imaging interval among the imaging intervals included in the progression information derived by the first analysis unit 23. The second analysis unit 24 derives the ratio of the number of similar reference images corresponding to the most common imaging interval to the number of all similar reference images. When the most common imaging interval is about six months, and the ratio of the number of similar reference images corresponding to an imaging interval that is about six months to the number of all similar reference images is 80%, the second analysis unit 24 derives as the statistical information about the imaging interval until the next imaging, information indicating that "80% of similar reference images have been acquired in six months".

As the statistical information about the doubling time of an abnormal shadow, the second analysis unit 24 derives the most common doubling time among the doubling times of the abnormal shadow included in the progression information derived by the first analysis unit 23. The second analysis unit 24 derives the ratio of the number of similar reference images corresponding to the most common doubling time to the number of all similar reference images. When the most common doubling time is about eight months, and the ratio of the number of similar reference images corresponding to a doubling time that is about eight months to the number of all similar reference images is 70%, the second analysis unit 24 derives as the statistical information about the doubling time of the abnormal shadow, information indicating that "the size has been doubled in eight months in 70% of similar reference images".

As the statistical information about a changing shape, the second analysis unit 24 derives the most common shape among changed shapes included in the progression information derived by the first analysis unit 23. The second analysis unit 24 derives the ratio of the number of similar reference images including the most common shape to the number of all similar reference images. When the ratio of the number of similar reference images including an abnormal shadow whose shape has changed to, for example, show spicula formation to the number of all similar reference images is 85%, the second analysis unit 24 derives as the statistical information about a changing shape, information indicating that "a change to show spicula formation is observed in 85% of similar reference images".

As the statistical information about a location where a new abnormal shadow appears, the second analysis unit 24 derives the most common location of appearance among locations where new abnormal shadows have appeared, the locations being included in the progression information derived by the first analysis unit 23. The second analysis unit 24 derives the ratio of the number of similar reference images including the most common location of appearance to the number of all similar reference images. When the most common location of appearance is the right upper lobe of the lung, and the ratio of the number of similar reference images in which the location of appearance is the right upper lobe of the lung to the number of all similar reference images is 75%, the second analysis unit 24 derives as the statistical information about a location where a new abnormal shadow appears, information indicating that "a new abnormal shadow appears in the right upper lobe of the lung in 75% of similar reference images".

As the statistical information about the name of a complication, the second analysis unit 24 derives the name of the most common complication among the names of complications included in the progression information derived by the first analysis unit 23. The second analysis unit 24 derives the ratio of the number of similar reference images corresponding to the name of the most common complication to the number of all similar reference images. When the name of the most common complication is cancer, and the ratio of the number of similar reference images in which cancer develops as a complication to the number of all similar reference images is 80%, the second analysis unit 24 derives as the statistical information about the name of a complication, information indicating that "cancer develops as a complication in 80% of similar reference images".

As the statistical information, the second analysis unit 24 may derive the number of pieces of corresponding information relative to the number of all similar reference images instead of the ratio. For example, regarding the statistical information about the name of a complication, when cancer develops as a complication in 80 similar reference images out of 100 similar reference images, the second analysis unit 24 may derive as the statistical information about the name of a complication, information indicating that "cancer develops as a complication in 80 similar reference images out of 100 similar reference images".

Figure 6:
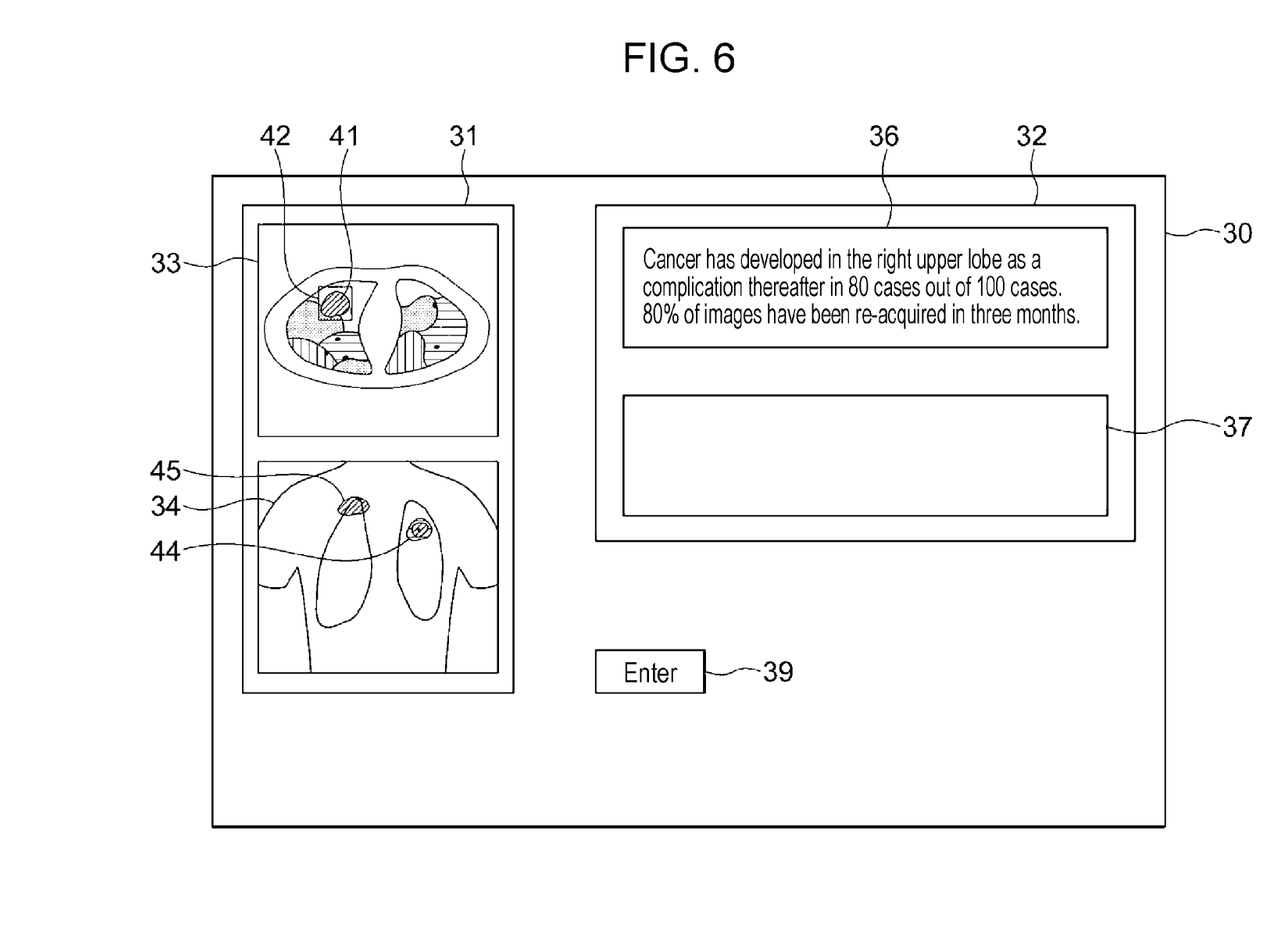
FIG. 6 is a diagram illustrating an example of a display screen for prediction information.

The display control unit 25 displays prediction information on the display 14. FIG. 6 is a diagram illustrating a display screen for prediction information. As illustrated in FIG. 6, a display screen 30 for prediction information includes an image display region 31 and a text display region 32. In the image display region 31, a tomographic image 33 showing a cross section of a target image is displayed so as to allow switching of the cross section. The tomographic image can be switched by, for example, using the wheel of the mouse included in the input device 15. The pixels of the target image are classified into a plurality of findings, and therefore, the display control unit 25 displays the target image while assigning different colors to the respective findings. FIG. 6 illustrates different colors as different hatching patterns. To simplify illustration, the number of findings in FIG. 6 is smaller than the actual number. In the image display region 31, a scout image 34 is displayed. The scout image 34 is an image for checking the full scope the photographic subject included in the target image. In the present embodiment, the target image is a three-dimensional image, and therefore, a tomographic image of a coronal plane obtained by dividing the human body in the right-left direction is displayed as the scout image 34.

The display control unit 25 highlights an abnormal shadow based on the result of classifying findings, in the tomographic image 33 and the scout image 34 displayed in the image display region 31. For example, the display control unit 25 highlights an abnormal shadow 41 in the tomographic image 33 by enclosing the abnormal shadow 41 in a rectangular region 42. The display control unit 25 highlights an abnormal shadow corresponding to the abnormal shadow highlighted in the tomographic image 33 with a heat map 44 in the scout image 34. The heat map 44 is colored differently depending on the degree of abnormality. In FIG. 6, the heat map 44 shows a part closer to the center of the abnormal shadow with a hatching pattern representing a darker color. The display control unit 25 highlights an area of a future abnormality that is predicted on the basis of the prediction information by adding a hatching pattern 45 in the scout image 34.

The text display region 32 of the display screen 30 includes a prediction information display region 36 and a finding display region 37. In the prediction information display region 36, prediction text based on the prediction information derived by the second analysis unit 24 is displayed. In FIG. 6, the prediction text displayed in the prediction information di splay region 36 reads "cancer has developed in the right upper lobe as a complication thereafter in 80 cases out of 100 cases, and 80% of images have been re-acquired in three months". Therefore, the hatching pattern 45 is added to the right upper lobe in the scout image 34.

Regarding conversion of prediction information to text, it is assumed that the display control unit 25 has a learning model subjected to learning so as to convert input information to text, and in response to input of prediction information, the learning model needs to output prediction text. As the learning model for converting prediction information to text, for example, a recurrent neural network can be used. In this case, the learning model needs to be created by machine-learning the recurrent neural network using prediction information and prediction text as training data.

Into the finding display region 37, findings discovered by the interpreting doctor interpreting the target image are entered. At this time, the interpreting doctor can enter the findings with reference to the prediction text displayed in the prediction information display region 36 by using the input device 15. Note that the display control unit 25 may have a learning model that detects an abnormal shadow from the target image and a learning model that generates a finding remark about the abnormal shadow. In this case, the display control unit 25 uses the learning models to generate a finding remark about an abnormal shadow included in the target image and displays the generated finding remark in the finding display region 37. Also in this case, the interpreting doctor can correct the finding remark with reference to the prediction text by using the input device 15.

Below the text display region 32 of the display screen 30, an enter button 39 is displayed. When the interpreting doctor selects the enter button 39, the content of the finding remark displayed in the finding display region 37 can be confirmed.

In response to selection of the enter button 39 by the operator, the saving control unit 26 copies the finding remark displayed in the finding display region 37 in the text display region 32 to an interpretation report and saves the interpretation report and the tomographic image referred to upon generation of the interpretation report in the storage 13 together.

The communication unit 27 transfers the interpretation report and the tomographic image referred to upon generation of the interpretation report to the report server 7 together via the network I/F 17. The report server 7 saves the interpretation report and the tomographic image together. At this time, the target image saved on the image server 5 and the interpretation report saved on the report server 7 are associated with each other and registered to the image DB 6 and the report DB 8.

Figure 7:
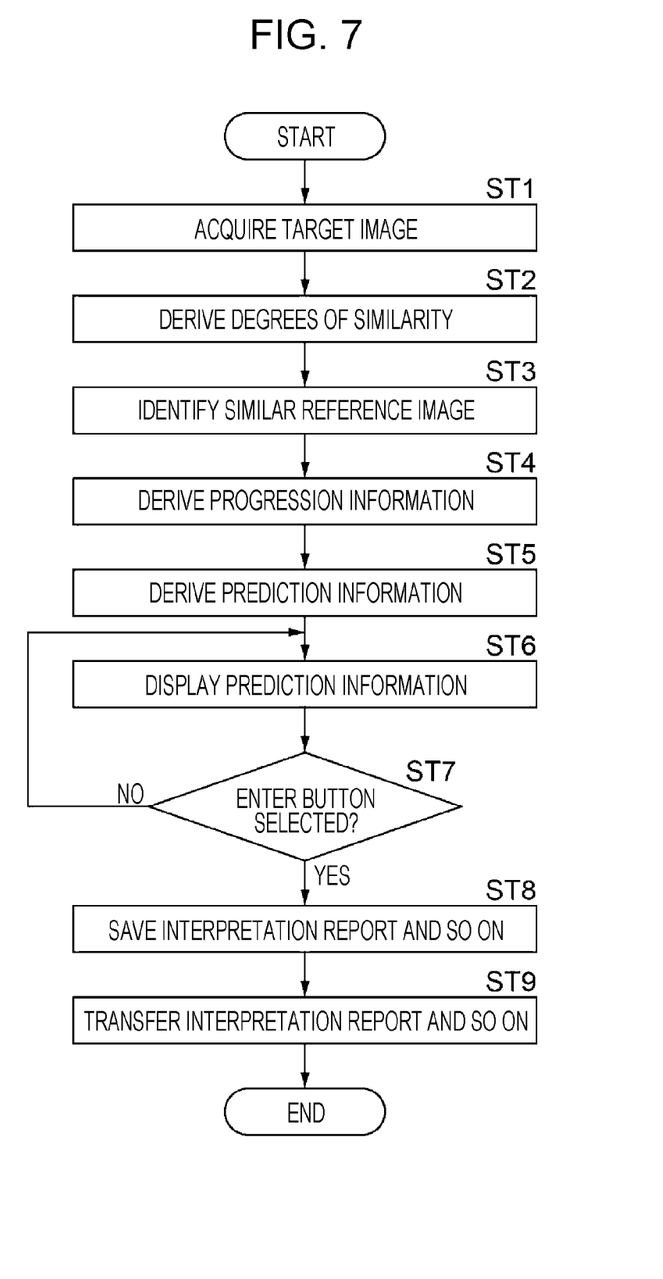
FIG. 7 is a flowchart illustrating a process performed in the present embodiment.

Next, a process performed in the present embodiment will be described. FIG. 7 is a flowchart illustrating the process performed in the present embodiment. In response to an interpreting doctor using the input device 15 and giving an instruction for acquiring a medical image that is to be interpreted, the process is started, and the information acquisition unit 21 acquires the target image (step ST1). Next, the degree-of-similarity deriving unit 22 derives the degrees of similarity between the target image and all reference images registered to the image DB 6 (step ST2). The first analysis unit 23 identifies a similar reference image, among the plurality of reference images registered to the image DB 6, having a degree of similarity greater than or equal to a predetermined threshold value (step ST3). The first analysis unit 23 analyzes an interpretation report about the similar reference image to thereby derive progression information about abnormal shadows included in the similar reference image (step ST4).

Subsequently, the second analysis unit 24 statistically analyzes the progression information derived by the first analysis unit 23 to thereby derive prediction information for predicting future progression of abnormal shadows included in the target image (step ST5). The display control unit 25 displays on the display 14, the display screen 30 for displaying the prediction information (prediction information display, step ST6). Accordingly, the interpreting doctor can enter a finding remark into the finding display region 37 with reference to prediction text based on the prediction information.

Subsequently, the display control unit 25 determines whether the enter button 39 is selected (step ST7). If the result of determination in step ST7 is "NO", the process returns to step ST6.

If the result of determination in step ST7 is "YES", the saving control unit 26 copies the entered finding remark to an interpretation report about the target image and saves the interpretation report and the target image in the storage 13 together (saving of interpretation report and so on, step ST8). The communication unit 27 transfers the interpretation report and the target image to the report server 7 via the network I/F 17 together (transfer of interpretation report and so on, step ST9), and the process ends.

As described above, in the present embodiment, progression information about a similar reference image having a degree of similarity with the target image that is a diagnosis target greater than or equal to a threshold value is derived, and the progression information is statistically analyzed to thereby derive prediction information for predicting future progression of abnormal shadows included in the target image. Accordingly, with reference to the prediction information, information about, for example, future changes in the abnormal shadows included in the target image and intervals at which an examination needs to be carried out in the future can be acquired. Therefore, according to the present embodiment, future progression of abnormal shadows in a medical image that is a diagnosis target can be predicted.

Note that although the degrees of similarity between one target image and reference images are derived to thereby identify a similar reference image in the embodiment described above, the present embodiment is not limited to this. For the same photographic subject, the target image and at least one past image acquired on an imaging date earlier than the imaging date of the target image may be used as one group (hereinafter referred to as "target image group") to derive the degrees of similarity with reference images. In this case, as the reference images, the degree-of-similarity deriving unit 22 first identifies a reference image group having an imaging interval corresponding to the imaging interval of the set of the target image and the past image and including a plurality of reference images that include the same photographic subject.

Here, "corresponding imaging interval" is an imaging interval that matches the imaging interval of the target image and the past image to some extent. "Some extent" may include an error of about ±10% of the length of the imaging interval. For example, when the imaging interval is six months, an error of about ±20 days may be included.

Figure 8:
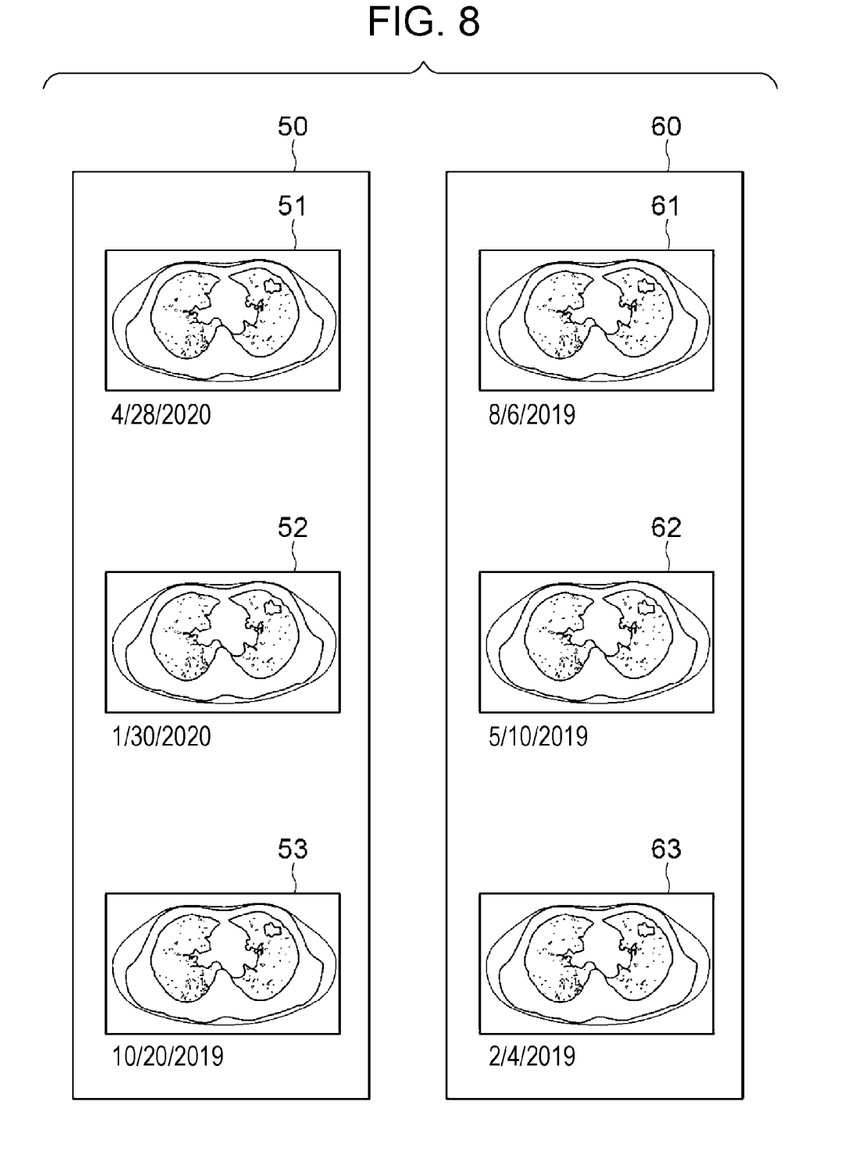
FIG. 8 is a diagram for explaining identification of a reference image group.

FIG. 8 is a diagram for explaining identification of a reference image group. FIG. 8 illustrates a target image group 50 that includes a target image 51 and two past images 52 and 53. The imaging date of the target image 51 is Apr. 28, 2020, and the imaging dates of the two past images 52 and 53 are Jan. 30, 2020 and Oct. 20, 2019 respectively. The imaging intervals of the three images 51 to 53 included in the target image group 50 are ab out three months. Therefore, the degree-of-similarity deriving unit 22 identifies a reference image group having an imaging interval of about three months and including three reference images that includes the same photographic subject. For example, as illustrated in FIG. 8, the degree-of-similarity deriving unit 22 identifies a reference image group 60 including three reference images 61 to 63 for which the imaging dates are Aug. 6, 2019, May 10, 2019, and Feb. 4, 2019 respectively. The degree-of-similarity deriving unit 22 identifies a plurality of reference image groups each having an imaging interval the same as the imaging interval of the target image group 50 from a plurality of reference images registered to the image DB 6.

The degree-of-similarity deriving unit 22 derives the degrees of similarity between the target image group and the reference image groups. Although each of the degrees of similarity may be derived between the target image and a reference image having the latest imaging date among the reference images included in the reference image group, the present embodiment is not limited to this. The degree of similarity between a past image included in the target image group and a reference image having the earliest imaging date among the reference images included in the reference image group may also be derived. Among the reference image groups, a reference image group similar to the target image group is referred to as "similar reference image group".

After the degree-of-similarity deriving unit 22 thus identifies the similar reference image group, the first analysis unit 23 analyzes an interpretation report about each of the plurality of similar reference images included in the similar reference image group to thereby derive progression information similarly to the embodiment described above. The second analysis unit 24 statistically analyzes the progression information derived similarly to the embodiment described above to thereby derive prediction information.

The reference image groups are not limited to those having imaging intervals each having a length that corresponds to the imaging intervals of the target image and past images included in the target image group. For example, in a case where the target image group includes the target image and two past images, the degree-of-similarity deriving unit 22 may identify as a reference image group, a similar reference image group from among reference image groups that each include three reference images having different imaging dates or same imaging date and different imaging times regardless of a length of the imaging intervals of the target image and the two past images.

In the embodiment described above, prediction information may be transmitted to and saved on the report server 7 together with the interpretation report. Accordingly, upon a diagnosis on the diagnosis-treatment WS 4 with reference to the interpretation report, the prediction about future abnormal shadows included in the target image is facilitated. This can make the diagnosis more appropriate.

Although the progression prediction apparatus according to the present disclosure is applied to the interpretation WS 3 in the embodiment described above, the present embodiment is not limited to this. The progression prediction apparatus according to the present disclosure may be applied to the diagnosis-treatment WS 4.

Although the technique of the present disclosure is applied to a case where an interpretation report is created for a medical image including a lung as a diagnosis target, which is a target image, in the embodiment described above, the diagnosis target is not limited to a lung. In addition to the lung, any area of a human body, such as the heart, the liver, the brain, or a limb, can be the diagnosis target.

In the embodiment described above, the hardware configuration of processing units, such as the information acquisition unit 21, the degree-of-similarity deriving unit 22, the first analysis unit 23, the second analysis unit 24, the display control unit 25, the saving control unit 26, and the communication unit 27, that perform various types of processing is implemented as various processors as described below. The various processors include, in addition to a CPU, which is a general-purpose processor executing software (program) to function as various processing units as described above, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One processing unit may be configured as one of the various processors or a combination of two or more processors of the same type or different types (for example, a combination of a plurality of FPGAs or a combination of a CPU and an FPGA). Further, a plurality of processing units may be configured as one processor.

As the first example of configuring a plurality of processing units as one processor, a form is possible where one or more CPUs and software are combined to configure one processor, and the processor functions as the plurality of processing units, representative examples of which include computers, such as a client and a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, as the hardware configuration of the various processors, more specifically, an electric circuit (circuitry) in which circuit elements, such as semiconductor elements, are combined can be used.

REFERENCE SIGNS LIST 1 medical information system
2 imaging apparatus
3 interpretation WS
4 diagnosis-treatment WS
5 image server
6 image DB
7 report server
8 report DB
10 network
11 CPU
12 progression prediction program
13 storage
14 display
15 input device
16 memory
17 network I/F
18 bus
20 progression prediction apparatus
21 information acquisition unit
22 degree-of-similarity deriving unit
23 first analysis unit
24 second analysis unit
25 display control unit
26 saving control unit
27 communication unit
30 display screen
31 image display region
32 text display region
33 tomographic image
34 scout image
36 prediction information display region
37 finding display region
39 enter button
41 abnormal shadow
42 rectangular region
44 heat map
45 hatching pattern
50 target image group
51 target image
52, 53 past image
60 reference image group
61 to 63 reference image
Rs0, Rr1 to Rr3 interpretation report
Ss0 similar reference image
Sr1 to Sr3 reference image

What is claimed is:

1. A progression prediction apparatus comprising:
   at least one processor,
   the processor being configured to
   derive, with reference to a database in which a plurality of reference images are saved such that an interpretation result about an abnormal shadow included in each reference image of the plurality of reference images is associated with the reference image, a degree of similarity between a target image and each of the plurality of reference images,
   analyze, for a similar reference image, among the plurality of reference images, for which the degree of similarity is greater than or equal to a predetermined threshold value, an interpretation result regarding the similar reference image to thereby derive progression information about an abnormal shadow included in the similar reference image, and
   statistically analyze the progression information to thereby derive prediction information for predicting future progression of an abnormal shadow included in the target image.

2. The progression prediction apparatus according to claim 1, wherein the prediction information includes at least one of a disease name, a change in size of the abnormal shadow, a change in shape of the abnormal shadow, presence or absence of an appearance of a new abnormal shadow, a location where the new abnormal shadow appears, a name of a complication that is likely to develop, or a period until a next diagnosis.

3. The progression prediction apparatus according to claim 1, wherein the processor is configured to display the prediction information on a display.

4. The progression prediction apparatus according to claim 2, wherein the processor is configured to display the prediction information on a display.

5. The progression prediction apparatus according to claim 4, wherein the processor is configured to, in a case where the prediction information includes the location where the new abnormal shadow appears, display the target image so as to highlight, in the displayed target image, the location where the new abnormal shadow appears.

6. The progression prediction apparatus according to claim 1, wherein the processor is configured to derive a feature value about the target image and derive the degree of similarity on the basis of the feature value derived for the target image and a feature value about each of the plurality of reference images.

7. The progression prediction apparatus according to claim 1, wherein
   the processor is configured to
   extract at least one related similar reference image associated with the same subject as the similar reference image, and
   analyze the interpretation result related to the similar reference image and the related similar reference image to thereby derive the progression information.

8. The progression prediction apparatus according to claim 7, wherein
   the similar reference image is associated with a first date, and
   the related similar reference image is associated with a second date different from the first date.

9. The progression prediction apparatus according to claim 8, wherein the second date is a later date relative to the first date.

10. The progression prediction apparatus according to claim 1, wherein the progression information includes at least one of an imaging interval, a doubling time of an abnormal shadow, a changed shape, a place where a new abnormal shadow appears, and a name of a complication.

11. The progression prediction apparatus according to claim 1, wherein
    the processor is configured to
    derive a degree of similarity between a target image group and each of reference image groups, the target image group including the target image and at least one past target image acquired on an imaging date earlier than an imaging date of the target image by imaging a photographic subject the same as a photographic subject for which the target image is acquired, each of the reference image groups including, among the plurality of reference images, a plurality of reference images acquired by imaging a same photographic subject and each having an imaging interval corresponding to imaging intervals of the target image and the at least one past target image, and
    analyze, for a similar reference image group for which the degree of similarity is greater than or equal to a predetermined threshold value, interpretation results associated with a plurality of similar reference images included in the similar reference image group to thereby derive progression information about the similar reference image group.

12. The progression prediction apparatus according to claim 1, wherein
    the processor is configured to
    obtain a plurality of the progression information, and
    statistically analyze the plurality of progression information to thereby derive the prediction information.

13. The progression prediction apparatus according to claim 1, wherein
    the processor is configured to
    derive a plurality of the progression information corresponding to the similar reference images respectively, and
    derive the prediction information based on the plurality of the progression information.

14. A progression prediction method comprising:
    deriving, with reference to a database in which a plurality of reference images are saved such that an interpretation result about an abnormal shadow included in each reference image of the plurality of reference images is associated with the reference image, a degree of similarity between a target image and each of the plurality of reference images;
    analyzing, for a similar reference image, among the plurality of reference images, for which the degree of similarity is greater than or equal to a predetermined threshold value, an interpretation result regarding the similar reference image to thereby derive progression information about an abnormal shadow included in the similar reference image; and
    statistically analyzing the progression information to thereby derive prediction information for predicting future progression of an abnormal shadow included in the target image.

15. A non-transitory computer recording medium storing a progression prediction program for causing a computer to perform:
    deriving, with reference to a database in which a plurality of reference images are saved such that an interpretation result about an abnormal shadow included in each reference image of the plurality of reference images is associated with the reference image, a degree of similarity between a target image and each of the plurality of reference images;

analyzing, for a similar reference image, among the plurality of reference images, for which the degree of similarity is greater than or equal to a predetermined threshold value, an interpretation result regarding the similar reference image to thereby derive progression information about an abnormal shadow included in the similar reference image; and statistically analyzing the progression information to thereby derive prediction information for predicting future progression of an abnormal shadow included in the target image.

* * * * *